United States Patent
Kodani et al.

(10) Patent No.: US 12,414,475 B2
(45) Date of Patent: Sep. 9, 2025

(54) PIEZOELECTRIC FILM HAVING A VINYLIDENEFLUORIDE/ TETRAFLUOROETHYLENE COPOLYMER FILM

(71) Applicant: DAIKIN INDUSTRIES, LTD., Osaka (JP)

(72) Inventors: Tetsuhiro Kodani, Osaka (JP); Saori Sakami, Osaka (JP); Shinya Bitou, Osaka (JP); Takashi Kanemura, Osaka (JP); Akinari Sugiyama, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 1070 days.

(21) Appl. No.: 17/285,778

(22) PCT Filed: Oct. 16, 2019

(86) PCT No.: PCT/JP2019/040565
§ 371 (c)(1),
(2) Date: Apr. 15, 2021

(87) PCT Pub. No.: WO2020/080382
PCT Pub. Date: Apr. 23, 2020

(65) Prior Publication Data
US 2021/0384411 A1    Dec. 9, 2021

(30) Foreign Application Priority Data

Oct. 16, 2018  (JP) .................. 2018-195261
Aug. 2, 2019   (JP) .................. 2019-143046

(51) Int. Cl.
*H01L 41/45*   (2013.01)
*H01L 41/193*  (2006.01)
(Continued)

(52) U.S. Cl.
CPC ......... *H10N 30/857* (2023.02); *H10N 30/045* (2023.02); *H10N 30/098* (2023.02)

(58) Field of Classification Search
CPC ... H10N 30/045; H10N 30/098; H10N 30/857
(Continued)

(56) References Cited

U.S. PATENT DOCUMENTS

2010/0068460 A1   3/2010   Moriyama et al.
2013/0122275 A1   5/2013   Moriyama et al.
(Continued)

FOREIGN PATENT DOCUMENTS

CN   106104825   11/2016
JP   61-102791   5/1986
(Continued)

OTHER PUBLICATIONS

Extended European Search Report issued Jul. 6, 2022, in corresponding European Patent Application No. 19873471.7.
(Continued)

*Primary Examiner* — Emily P Pham
*Assistant Examiner* — Monica Mata
(74) *Attorney, Agent, or Firm* — Wenderoth, Lind & Ponack, L.L.P.

(57) ABSTRACT

An object is to provide a piezoelectric film with good piezoelectricity. This object can be achieved by a piezoelectric film comprising a vinylidene fluoride/tetrafluoroethylene copolymer film and having a residual polarization amount of 40 mC/m² or more.

15 Claims, 1 Drawing Sheet

(51) Int. Cl.
     *H01L 41/257*    (2013.01)
     *H10N 30/045*    (2023.01)
     *H10N 30/098*    (2023.01)
     *H10N 30/857*    (2023.01)

(58) Field of Classification Search
     USPC .......................................................... 310/357
     See application file for complete search history.

(56) References Cited

U.S. PATENT DOCUMENTS

| | | |
|---|---|---|
| 2017/0033276 A1 | 2/2017 | Kou et al. |
| 2020/0144481 A1* | 5/2020 | Bitou .................... H10N 30/302 |
| 2020/0303619 A1* | 9/2020 | Kodani ................ H10N 30/302 |

FOREIGN PATENT DOCUMENTS

| | | |
|---|---|---|
| JP | 2008-171935 | 7/2008 |
| JP | 2016-219804 | 12/2016 |
| WO | 2015/053346 | 4/2015 |
| WO | 2017/170616 | 10/2017 |

OTHER PUBLICATIONS

English Translation of the International Preliminary Report on Patentability issued Apr. 14, 2021 in International (PCT) Application No. PCT/JP2019/040565.

International Search Report issued Dec. 24, 2019 in International (PCT) Application No. PCT/JP2019/040565.

\* cited by examiner

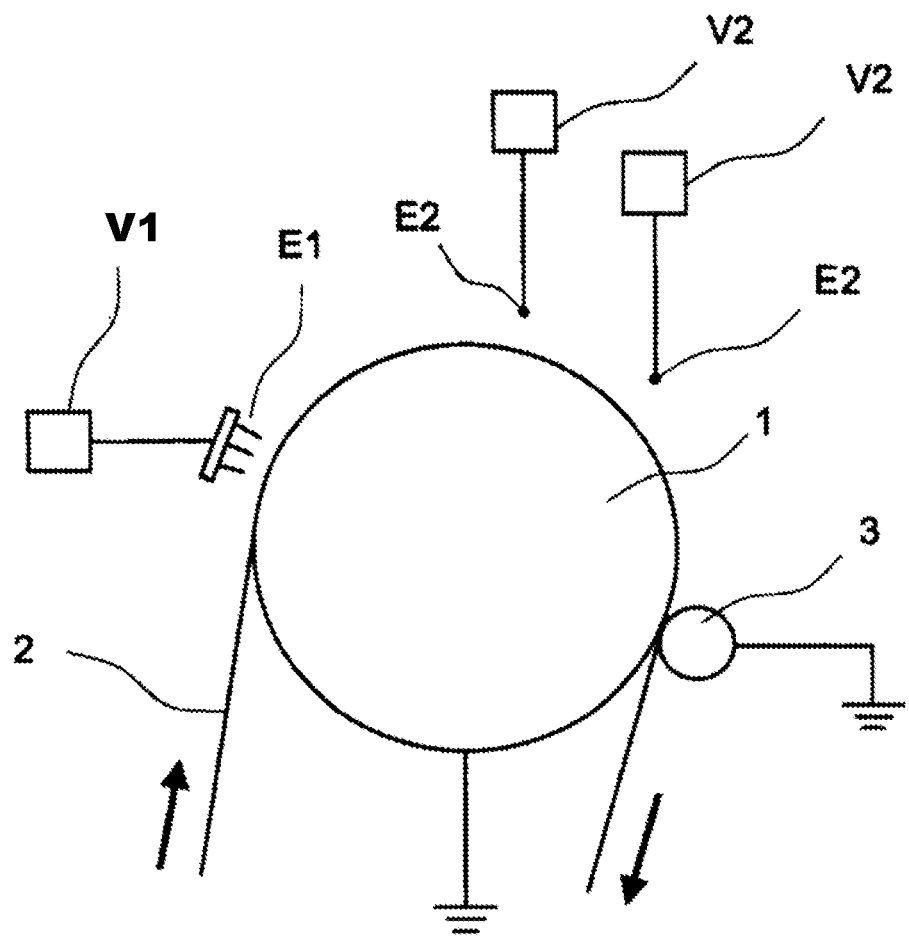

PIEZOELECTRIC FILM HAVING A VINYLIDENEFLUORIDE/ TETRAFLUOROETHYLENE COPOLYMER FILM

TECHNICAL FIELD

The present disclosure relates to a piezoelectric film.

BACKGROUND ART

Piezoelectric films are films that have piezoelectricity (the property of converting applied force into voltage, or the property of converting applied voltage into force). Piezoelectric films are used in various applications that utilize piezoelectricity (e.g., sensors, actuators, touch panels, haptic devices (devices that have the ability to feed back tactile sensations to users), vibration power generators, speakers, and microphones).

Polyvinylidene fluoride (PVDF) films are typically used as piezoelectric films. In order to impart good piezoelectricity to PVDF films, it is necessary to uniaxially stretch the PVDF films and apply polarization treatment (e.g., PTL 1).

It has also been proposed to use a vinylidene fluoride/tetrafluoroethylene copolymer film as a piezoelectric film (e.g., PTL 2).

CITATION LIST

Patent Literature

PTL 1: JP2008-171935A
PTL 2: JP2016-219804A

SUMMARY OF INVENTION

Technical Problem

However, uniaxially stretched PVDF films shrink due to heat, and piezoelectricity is reduced. Therefore, when PVDF films are used for piezoelectric materials whose production process includes heat treatment, the reduction of piezoelectricity is a particular problem.

In addition, since vinylidene fluoride/tetrafluoroethylene copolymer films have lower piezoelectricity than PVDF films, further improvement in piezoelectricity is required.

An object of the present disclosure is to provide a piezoelectric film with good piezoelectricity.

Solution to Problem

The present disclosure includes the following embodiments.

Item 1.
A piezoelectric film comprising a vinylidene fluoride/tetrafluoroethylene copolymer film and having a residual polarization amount of 40 mC/m$^2$ or more.

Item 2.
The piezoelectric film according to Item 1, wherein the residual polarization amount is 45 mC/m$^2$ or more.

Item 3.
The piezoelectric film according to Item 1 or 2, wherein the ratio of internal haze value [%]/film thickness [μm] is more than 1.0.

Item 4.
The piezoelectric film according to any one of Items 1 to 3, wherein the ratio of internal haze value [%]/film thickness [μm] is 1.1 or more.

Item 5.
The piezoelectric film according to any one of Items 1 to 4, which has an internal haze value of more than 30%.

Item 6.
The piezoelectric film according to any one of Items 1 to 5, which has an internal haze value of 40% or more.

Item 7.
The piezoelectric film according to any one of Items 1 to 6, which has an internal haze value of 45% or more.

Item 8.
The piezoelectric film according to any one of Items 1 to 7, which has an area of 9 cm$^2$ or more.

Item 9.
The piezoelectric film according to any one of Items 1 to 8, wherein the residual polarization amount is 50 mC/m$^2$ or more, the internal haze value is within the range of more than 50% and 80% or less, and the area is 9 cm$^2$ or more.

Item 10.
The piezoelectric film according to any one of Items 1 to 9, which has a degree of crystallinity of 50% or more, the degree of crystallinity being expressed by 100×(area of crystalline peak)/(sum of area of crystalline peak and area of amorphous halo peak), wherein in an X-ray diffraction pattern obtained by placing a film sample directly on a sample holder with an aperture, and performing X-ray diffraction measurement at a diffraction angle 2θ of 10 to 40°, a baseline is set as a straight line connecting a diffraction intensity at a diffraction angle 2θ of 10° and a diffraction intensity at a diffraction angle 2θ of 25°, an area surrounded by the baseline and a diffraction intensity curve is separated into two symmetric peaks by profile fitting, and of these peaks, the one with a larger diffraction angle 2θ is recognized as the crystalline peak, and the one with a smaller diffraction angle 2θ is recognized as the amorphous halo peak.

Item 11.
The piezoelectric film according to Item 10, wherein the degree of crystallinity is 55% or more.

Item 12.
The piezoelectric film according to any one of Items 1 to 11, wherein the variation coefficient of thickness is 10% or less when the thickness is measured at 10 points every square centimeter over the entire film in a plane direction.

Item 13.
The piezoelectric film according to any one of Items 1 to 12, which has a piezoelectric constant $d_{33}$ of 15 pC/N or more.

Item 14.
The piezoelectric film according to any one of Items 1 to 13, which has a thickness of 5 to 3000 μm.

Item 15.
The piezoelectric film according to any one of Items 1 to 14, which has an internal haze value within the range of 60 to 80%.

Item 16.
The piezoelectric film according to any one of Items 1 to 15, which has an internal haze value within the range of 65 to 80%.

Item 17.
The piezoelectric film according to any one of Items 1 to 16, wherein in the vinylidene fluoride/tetrafluoroethylene copolymer, the molar ratio of repeating units derived from vinylidene fluoride and repeating units derived from tetrafluoroethylene is within the range of 60/40 to 97/3.

Item 18.
The piezoelectric film according to any one of Items 1 to 17, wherein the ratio of retardation [nm]/film thickness [μm] is within the range of 0.02 to 2.5.
Item 19.
The piezoelectric film according to any one of Items 1 to 18, for use in one or more members selected from the group consisting of sensors, actuators, touch panels, haptic devices, vibration power generators, speakers, and microphones.
Item 20.
A piezoelectric material that is a laminate, the piezoelectric material comprising:
the piezoelectric film according to any one of Items 1 to 18, and
an electrode provided on at least one surface of the piezoelectric film.

The present disclosure also includes the following embodiments.
A method for producing a piezoelectric film, comprising:
(1) preparing a liquid composition congaing a vinylidene fluoride/tetrafluoroethylene copolymer and a solvent;
(2) applying the liquid composition to a substrate; and
(3) exposing the substrate, to which the liquid composition has been applied, to a predetermined temperature to form a film.
The above production method, wherein step (3) is a step of exposing the substrate to a temperature within the range of 150 to 200° C. for less than 1 hour, and then to a temperature within the range of 110° C. or more and less than 150° C. for 5 hours or more.

Advantageous Effects of Invention

The present disclosure provides a piezoelectric film with good piezoelectricity.

BRIEF DESCRIPTION OF DRAWING

FIG. 1 is a schematic diagram showing the outline of a production device used to produce the piezoelectric films of Examples.

DESCRIPTION OF EMBODIMENTS

The above overview of the present disclosure is not intended to describe each of the disclosed embodiments or all implementations of the present disclosure.
The following description of the present disclosure more specifically exemplifies the embodiments of the examples.
Guidance is provided through examples in several parts of the present disclosure, and these examples can be used in various combinations.
In each case, the group of examples can function as a non-exclusive and representative group.
All publications, patents, and patent applications cited herein are incorporated herein by reference in their entirety.

Terms

Unless otherwise specified, the symbols and abbreviations in the present specification can be understood in the context of the present specification in the meaning commonly used in the technical field to which the present disclosure belongs.
In the present specification, the terms "comprise" and "contain" are used with the intention of including the teams "consisting essentially of" and "consisting of."
Unless otherwise specified, the steps, treatments, or operations described in the present specification may be performed at room temperature.
In the present specification, room temperature can refer to a temperature within the range of 10 to 40° C.
In the present specification, the phrase "$C_{n-m}$" (n and m are each a number) indicates that the number of carbon atoms is n or more and m or less, as can be generally understood by a person skilled in the art.

Piezoelectric Film

The piezoelectric film according to one embodiment of the present disclosure comprises a vinylidene fluoride/tetrafluoroethylene copolymer film.
In the vinylidene fluoride/tetrafluoroethylene copolymer, the molar ratio of repeating units derived from vinylidene fluoride ($—CH_2—CF_2—$) and repeating units derived from tetrafluoroethylene ($—CF_2—CF_2—$) is not limited, and can be within the range of, for example, 50/50 to 99/1. The molar ratio is preferably within the range of 60/40 to 97/3, more preferably within the range of 65/35 to 95/5, and particularly preferably within the range of 70/30 to 90/10, in terms of improving the dimensional stability due to heat.
The vinylidene fluoride/tetrafluoroethylene copolymer may be a copolymer consisting of vinylidene fluoride and/or tetrafluoroethylene, or a copolymer consisting essentially of vinylidene fluoride and/or tetrafluoroethylene.
The vinylidene fluoride/tetrafluoroethylene copolymer may also contain a comonomer copolymerizable with vinylidene fluoride and/or tetrafluoroethylene. This comonomer may have an ethylenically unsaturated double bond.
Specific examples of the comonomer include:
fluorine-containing monomers, such as vinyl fluoride (VF), trifluoroethylene (TrFE), hexafluoropropene (HFP), 1-chloro-1-fluoroethylene (1,1-CFE), 1-chloro-2-fluoroethylene (1,2-CFE), 1-chloro-2,2-difluoroethylene (CDFE), chlorotrifluoroethylene (CTFE), trifluorovinyl monomer, 1,1,2-trifluorobutene-4-bromo-1-butene, 1,1,2-trifluorobutene-4-silane-1-butene, perfluoropropyl vinyl ether (PPVE), perfluoroacrylate, 2,2,2-trifluoroethylacryllate, and 2-(perfluorohexyl) ethyl acrylate;
fluorine-free monomers, such as α-olefins (e.g., ethylene and propylene), unsaturated dicarboxylic acids or derivatives thereof (e.g., maleic acid and maleic anhydride), vinyl ethers (e.g., ethyl vinyl ether), allyl ethers (e.g., allyl glycidyl ether), vinyl esters (e.g., vinyl acetate), acrylic acid or esters thereof, and methacrylic acid or esters thereof; and
combinations of one or two or more of these.
The vinylidene fluoride/tetrafluoroethylene copolymer may contain repeating units derived from the comonomer in an amount of, for example, 10 mol % or less, and preferably within the range of 0.01 to 5 mol %, in the repeating units derived from all the monomers.
The vinylidene fluoride/tetrafluoroethylene copolymer is preferably a polarized vinylidene fluoride/tetrafluoroethylene copolymer. In the present specification, the term "polarized" means that electric charges are placed on the surface. That is, the polarized vinylidene fluoride/tetrafluoroethylene copolymer can be an electret.
The piezoelectric film can contain additives commonly used in resin films. Specific examples of additives include fillers (e.g., inorganic oxide particles), affinity improvers, heat stabilizers, UV absorbers, pigments, and combinations of one or two or more of these. Preferable examples include inorganic oxide particles, and combinations of inorganic oxide particles and affinity improvers.

Preferable examples of inorganic oxide particles include at least one member selected from the group consisting of inorganic oxide particles (B1) to (B3) described below.

Inorganic oxide particles (61): particles of oxides of metal elements of Group 2, 3, 4, 12, or 13 of the periodic table, and inorganic oxide composite particles thereof.

Examples of the metal elements include Be, Mg, Ca, Sr, Ba, Y, Ti, Zr, Zn, and Al.

Preferable examples of (B1) include particles of oxides of Be, Al, Mg, Y, and Zr. These particles are preferable because they are versatile and inexpensive, and have high volume resistivity.

More preferable examples of (B1) include particles of at least one inorganic oxide selected from the group consisting of $AlO_3$, $MgO$, $ZrO_2$, $Y_2O_3$, $BeO$, and $MgO \cdot Al_2O_3$. These particles are preferable because they have high volume resistivity.

Even more preferable examples of (B1) include $Al_2O_3$ having a γ-type crystal structure. These particles are preferable because they have a large specific surface area and good dispersibility in the vinylidene fluoride/tetrafluoroethylene copolymer.

Inorganic oxide particles (B2): particles of inorganic composite oxides represented by formula: $M^1_{a1}M^2_{b1}O_{c1}$, wherein $M^1$ is a Group 2 metal element, $M^2$ is a Group 4 metal element, a1 is within the range of 0.9 to 1.1, b1 is within the range of 0.9 to 1.1, c1 is within the range of 2.8 to 3.2, and $M^1$ and $M^2$ each can be one or two or more metal elements.

Preferable examples of the Group 2 metal element include Mg, Ca, Sr, and Ba.

Preferable examples of the Group 4 metal element include Ti and Zr.

Preferable examples of (B2) include particles of at least one inorganic oxide selected from the group consisting of $BaTiO_3$, $SrTiO_3$, $CaTiO_3$, $MgTiO_3$, $BaZrO_3$, $SrZrO_3$, $CaZrO_3$, and $MgZrO_3$. These particles are preferable because they have high volume resistivity.

Inorganic oxide particles (B3): particles of oxides of metal elements of Group 2, 3, 4, 12, or 13 of the periodic table, and inorganic oxide composite particles of silicon oxide.

Examples of the metal elements include Be, Mg, Ca, Sr, Ba, Y, Ti, Zr, Zn, and Al.

Specific examples of (B3) include particles of at least one inorganic oxide selected from the group consisting of $3Al_2O_3 \cdot 2SiO_2$, $2MgO-SiO_2$, $ZrO_2 \cdot SiO_2$, and $MgO \cdot SiO_2$.

The inorganic oxide particles are not necessarily required to be highly dielectric, and can be appropriately selected depending on the use of the piezoelectric film. For example, versatile and inexpensive inorganic oxide particles (e.g., (B1), particularly $Al_2O_3$ particles and MgO particles) can be used to improve the volume resistivity. The relative permittivity (1 kHz, 25° C.) of a single type of these inorganic oxide particles (B1) is generally less than 100, and preferably within the range of 10 or less.

As the inorganic oxide particles, inorganic oxide particles (e.g., (B2) and (B3)) with ferroelectricity (e.g., a relative permittivity (1 kHz, 25° C.) of 100 or more) may be used for the purpose of improving the permittivity. Inorganic materials that form ferroelectric inorganic oxide particles include, but are not limited to, composite metal oxides, their complexes, solid solutions, and sol-gel forms.

The relative permittivity (25° C., 1 kHz) of the inorganic oxide particles is preferably within the range of 10 or more. From the standpoint of increasing the permittivity of the piezoelectric film, the relative permittivity is preferably within the range of 100 or more, and more preferably 300 or more. The upper limit of the relative permittivity is not limited, and is generally about 3000.

The relative permittivity (ε) (25° C., 1 kHz) of the inorganic oxide particles is a value calculated from the capacitance (C) measured using an LCR meter, electrode area (S), and sintered body thickness (d) using the formula $C = \varepsilon \varepsilon_0 \times S/d$ ($\varepsilon_0$: permittivity of vacuum).

The average primary particle size of the inorganic oxide particles is preferably small, and so-called nanoparticles having an average primary particle size of 1 μm or less are particularly preferable. Because such inorganic oxide nanoparticles are uniformly dispersed, the electrical insulating properties of the film can be significantly improved by incorporating a small amount of the inorganic oxide nanoparticles. The average primary particle size is preferably within the range of 800 nm or less, more preferably 500 nm or less, and even more preferably 300 nm or less. The average primary particle size is preferably within the range of 10 nm or more, more preferably 20 nm or more, and even more preferably 50 nm or more, in terms of difficulty in production, difficulty in uniform dispersion, and cost.

The average primary particle size of the inorganic oxide particles is calculated using a laser diffraction/scattering type particle size distribution measuring device (trade name: LA-920, HORIBA, Ltd.) or a similar instrument.

The piezoelectric film preferably contains the inorganic oxide particles in an amount within the range of 0.01 to 300 parts by mass, and more preferably 0.1 to 100 parts by mass, based on 100 parts by mass of the vinylidene fluoride/tetrafluoroethylene copolymer.

The lower limit of the content of the inorganic oxide particles is preferably 0.1 parts by mass, more preferably 0.5 parts by mass, and even more preferably 1 part by mass, from the standpoint of improving the electrical insulation properties.

The upper limit of the content of the inorganic oxide particles is preferably 200 parts by mass, more preferably 150 parts by mass, and even more preferably 100 parts by mass, from the standpoint of uniformly dispersing the inorganic oxide particles in the copolymer and preventing a decrease in the electrical insulation properties (withstand voltage) and a decrease in the tensile strength of the film.

When high total light transmittance and a low total haze value are required for the piezoelectric film, the content of the inorganic oxide particles is preferably lower, and more preferably zero.

When the piezoelectric film contains the inorganic oxide particles, the piezoelectric film may further contain an affinity improver.

The affinity improver can increase the affinity between the inorganic oxide particles and the copolymer, uniformly disperse the inorganic oxide particles in the copolymer, firmly bond the inorganic oxide particles and the copolymer in the film to suppress the formation of voids, and increase the relative permittivity.

Specific examples of the affinity improver include coupling agents, surfactants, and epoxy group-containing compounds.

Examples of coupling agents include organic titanium compounds, organic silane compounds, organic zirconium compounds, organic aluminum compounds, and organic phosphorus compounds.

Examples of organic titanium compounds include organic titanium coupling agents (e.g., alkoxy titanium, titanium chelate, and titanium acylate). Specific examples include tetraisopropyl titanate, titanium isopropoxyoctylene glycolate, diisopropoxy-bis(acetylacetonato)titanium, diisopropoxytitanium diisostearate, tetraisopropylbis(dioctylphosphite)titanate, isopropyltri(n-aminoethyl-aminoethyl)titanate, and tetra(2,2-diallyloxymethyl-1-butyl)bis(di-tridecyl)phosphite titanate.

Preferable examples of organic titanium compounds include alkoxytitanium and titanium chelate because of their good affinity with inorganic oxide particles.

The organic silane compound may be of a high-molecular-weight type or a low-molecular-weight type. Examples include alkoxysilanes (e.g., monoalkoxysilane, dialkoxysilane, trialkoxysilane, and tetraalkoxysilane), vinylsilanes, epoxysilanes, aminosilanes, metachioroxysilanes, and mercaptosilanes. When alkoxysilane is used, hydrolysis can further improve the volume resistivity (i.e., improve the electrical insulation properties), which is the effect of surface treatment.

Examples of organic zirconium compounds include alkoxyzirconium and zirconium chelate.

Examples of organic aluminum compounds include alkoxyaluminum and aluminum chelate.

Examples of organic phosphorus compounds include phosphite esters, phosphate esters, and phosphate chelates.

The surfactant as the affinity improver may be of a high-molecular-weight type or a low-molecular-weight type, but is preferably of a high-molecular-weight type, in terms of thermal stability.

Examples of the surfactant include nonionic surfactants, anionic surfactants, and cationic surfactants.

Examples of nonionic surfactants include polyether derivatives, polyvinylpyrrolidone derivatives, and alcohol derivatives. Preferable examples includes polyether derivatives because of their good affinity with the inorganic oxide particles.

Examples of anionic surfactants include polymers containing a sulfonic acid, a carboxylic acid, or a salt thereof. Preferable examples includes acrylic acid derivative polymers and methacrylic acid derivative polymers because of their good affinity with the copolymer.

Examples of cationic surfactants include amine compounds, compounds having a nitrogen-containing complex ring (e.g., imidazoline), and halogenated salts thereof.

The epoxy group-containing compound as the affinity improver may be a low-molecular-weight compound or a high-molecular-weight compound. Specific examples include epoxy compounds and glycidyl compounds, and preferable examples include low-molecular-weight compounds having one epoxy group, in terms of affinity with the copolymer.

More preferable examples of the epoxy group-containing compound include compounds represented by the following formula:

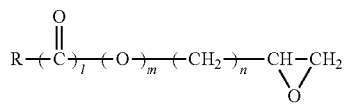

wherein R is a hydrogen atom, a methyl group, a $C_{2-10}$ hydrocarbon group optionally intervening an oxygen atom or a nitrogen atom, or an optionally substituted aromatic ring group; l is 0 or 1; m is 0 or 1; and n is an integer of 0 to 10.

Examples of the compound represented by the above formula include compounds having a ketone group or an ester group, and more specifically compounds represented by the following formulas:

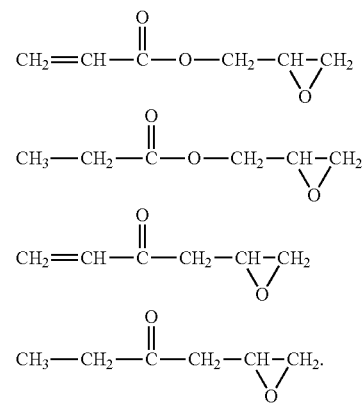

The content of the affinity improver can be preferably within the range of 0.01 to 30 parts by mass, more preferably 0.1 to 25 parts by mass, and even more preferably 1 to 20 parts by mass, based on 100 parts by mass of the inorganic oxide particles, in terms of uniform dispersion and the height of the relative permittivity of the resulting film.

The piezoelectric film can be a stretched or unstretched piezoelectric film, and is preferably an unstretched piezoelectric film.

Residual Polarization Amount
Method for Determining Residual Polarization Amount A sample film is obtained by patterning an aluminum electrode (flat electrode) by vacuum deposition on the center (5 mm×5 mm) of the film cut to 20 mm×20 mm, and then attaching two lead electrodes (3 mm×80 mm) made of aluminum foil reinforced with insulating tape to the flat electrode with conductive double-sided tape. The sample film, a function generator, a high-voltage amplifier, and an oscilloscope are incorporated into a Sawyer-Tower circuit, and a triangular wave is applied to the sample film (maximum: ±10 kV). The response of the sample film is measured using the oscilloscope to obtain the residual polarization amount at an applied electric field of 120 MV/m.

The residual polarization amount of the piezoelectric film is 40 mC/m² or more.

The lower limit of the residual polarization amount can be, for example, 45 mC/m², preferably 48 mC/m², more preferably 50 mC/m², and even more preferably 52 mC/m², in terms of further improving piezoelectricity.

The upper limit of the residual polarization amount can be, for example, 80 mC/m², 75 mC/m², or 70 mC/m².

The residual polarization amount can be, for example, within the range of 48 to 80 mC/m², within the range of 50 to 80 mC/m², within the range of 52 to 80 mC/m², or within the range of 55 to 80 mC/m².

Internal Haze Value
Method for Determining Internal Haze Value

In the present specification, the "internal haze value" (inner haze) is obtained according to ASTM D1003 in a haze (turbidity) test using a haze meter (product name: NDH7000SP CU2II, Nippon Denshoku Industries Co., Ltd.) or a similar instrument, in which the film is inserted into a glass cell filled with water, and the haze value is measured.

The internal haze value of the piezoelectric film is preferably more than 30%, more preferably 35% or more, even more preferably 40% or more, still even more preferably 45% or more, particularly preferably 50% or more, and more particularly preferably more than 50%, in terms of piezoelectricity.

The lower limit of the internal haze value of the piezoelectric film can be preferably 55%, 60%, 65%, or 70%, in terms of further improving piezoelectricity.

The upper limit of the internal haze value of the piezoelectric film can be, for example, 80% or 75%.

The internal haze value of the piezoelectric film can be, for example, within the range of more than 50% and 80% or less, within the range of 55 to 80%, within the range of 60 to 80%, within the range of 65 to 80%, or within the range of 70 to 80%.

Ratio of Internal Haze Value [%]/Film Thickness [μm]

The ratio of internal haze value [%]/film thickness [μm] of the piezoelectric film is preferably more than 1.0, and more preferably 1.1 or more.

Further, the ratio of internal haze value [%]/film thickness [μm] of the piezoelectric film is generally 2.0 or less, and preferably 1.9 or less.

The ratio of internal haze value [%]/film thickness [μm] of the piezoelectric film can be, for example, within the range of more than 1.0 and 2.0 or less, or within the range of 1.1 or more and 1.9 or less.

Area

The area of the piezoelectric film is preferably within the range of 9 cm$^2$ or more, in terms of industrial productivity. This range generally corresponds to the range of the area of a film produced by a roll-to-roll process.

The lower limit of the area of the piezoelectric film can be preferably 10 cm$^2$, 50 cm$^2$, 100 cm$^2$, 200 cm$^2$, 300 cm$^2$, 320 cm$^2$, 400 cm$^2$, 500 cm$^2$, 600 cm$^2$, 700 cm$^2$, 800 cm$^2$, 900 cm$^2$, 1000 cm$^2$, 1100 cm$^2$, 1200 cm$^2$, 1300 cm$^2$, 1400 cm$^2$, 1500 cm$^2$, or 1600 cm$^2$.

The upper limit of the area of the piezoelectric film can be, for example, 4000 m$^2$, 3500 m$^2$, 3000 m$^2$, 2500 m$^2$, 2000 m$^2$, 1500 m$^2$, 1000 m$^2$, or 500 m$^2$.

The area of the piezoelectric film can be, for example, within the range of 10 cm$^2$ to 4000 m$^2$, within the range of 100 cm$^2$ to 2000 m$^2$, or within the range of 600 cm$^2$ to 500 m$^2$.

In the piezoelectric film, preferable combinations of the residual polarization amount, internal haze value, and area are as follows:
 (a) a combination in which the residual polarization amount is 45 mC/m$^2$ or more, the internal haze value is more than 30%, and the area is 9 cm$^2$ or more;
 (b) a combination in which the residual polarization amount is 45 mC/m$^2$ or more, the ratio of internal haze value [%]/film thickness [μm] is more than 1.0, and the area is 9 cm$^2$ or more;
 (c) a combination in which the residual polarization amount is 45 mC/m$^2$ or more, the internal haze value is more than 30%, the ratio of internal haze value [%]/film thickness [μm] is more than 1.0, and the area is 9 cm$^2$ or more; and
 (d) a combination in which the residual polarization amount is 50 mC/m$^2$ or more, the internal haze value is within the range of more than 50% and 80% or less, and the area is 9 cm$^2$ or more.

Degree of Crystallinity

Method for Determining Degree of Crystallinity

In an X-ray diffraction pattern obtained by placing the film sample directly on a sample holder with an aperture, and performing X-ray diffraction measurement at a diffraction angle 2θ of 10 to 40°, a baseline is set as a straight line connecting a diffraction intensity at a diffraction angle 2θ of 10° and a diffraction intensity at a diffraction angle 2θ of 25°, and the area surrounded by the baseline and a diffraction intensity curve is separated into two symmetric beaks by profile fitting. Of these peaks, the one with a larger diffraction angle 2θ is recognized as a crystalline peak, and the one with a smaller diffraction angle 2θ is recognized as an amorphous halo peak. Under these conditions, the value expressed by 100×(area of crystalline peak)/(sum of area of crystalline peak and area of amorphous halo peak) is defined as the degree of crystallinity.

The lower limit of the degree of crystallinity of the piezoelectric film can be preferably 50% or 55%, in terms of piezoelectricity.

The lower limit of the degree of crystallinity can be preferably 60%, 65%, or 70%, in terms of dimensional stability due to heat and piezoelectricity.

The upper limit of the degree of crystallinity can be preferably 75%, 70%, 65%, or 60%.

The degree of crystallinity can be, for example, within the range of 50 to 80%, within the range of 55 to 80%, within the range of 60 to 80%, within the range of 65 to 80%, or within the range of 70 to 80%.

Piezoelectric Constant

Method for Determining Piezoelectric Constant

The piezoelectric constant $d_{33}$ is measured using a piezometer system (PM300 from Piezotest, to which a pin with a 1.5-mm-diameter tip is attached as a sample-fixing jig) or a similar instrument. The piezoelectric constant $d_{33}$ is measured at 10 non-arbitrarily selected points on the film, and the arithmetic mean value thereof is taken as the piezoelectric constant $d_{33}$. Selecting 10 non-arbitrary points on the film can be performed, for example, by selecting 10 points at 50-mm intervals on a straight line. The term "arbitrary" means that the variation coefficient, described later, is intended to be small.

The actual measured value of the piezoelectric constant $d_{33}$ is positive or negative depending on the front or back of the film to be measured. In the present specification, the absolute value is described as the value of the piezoelectric constant $d_{33}$.

The preferable lower limit of the piezoelectric constant $d_{33}$ of the piezoelectric film can be, for example, 15 pC/N, 17 pC/N, 18 pC/N, or 19 pC/N.

The preferable upper limit of the piezoelectric constant $da_3$ of the piezoelectric film can be, for example, 35 pC/N, 30 pC/N, 28 pC/N, 26 pC/N, or 20 pC/N.

The piezoelectric constant $d_{33}$ of the piezoelectric film can be, for example, within the range of 15 to 35 pC/N, within the range of 17 to 35 pC/N, within the range of 18 to 35 pC/N, or within the range of 19 to 35 pC/N.

Variation Coefficient of Piezoelectric Constant $d_{33}$

The variation coefficient of the piezoelectric constant $d_{33}$ of the piezoelectric film is the ratio of the standard deviation of the piezoelectric constant $d_{33}$ to the arithmetic mean.

The lower limit of the variation coefficient can be, for example, 0.0001, preferably 0.001, more preferably 0.01, and even more preferably 0.02, in terms of production costs.

The upper limit of the variation coefficient can be, for example, 2.0, preferably 1.0, more preferably 0.6, even more preferably 0.4, still even more preferably 0.3, and particularly preferably 0.15, in terms of in-plane uniformity.

The variation coefficient can be, for example, within the range of 0.01 to 1.0, within the range of 0.01 to 0.6, within the range of 0.01 to 0.5, within the range of 0.01 to 0.4, or within the range of 0.01 to 0.3.

Film Thickness

Method for Determining Film Thickness

In the present specification, the arithmetic mean value of the thicknesses measured at 10 non-arbitrarily selected points on the film is defined as the film thickness of the film.

The lower limit of the film thickness of the piezoelectric film can be, for example, 5 μm, 9 μm, or 10 μm.

The upper limit of the film thickness of the piezoelectric film can be, for example, 3000 μm, 2500 μm, 2000 μm, 1500 μm, 1000 μm, 800 μm, 500 μm, 200 μm, 100 μm, or 60 μm.

The film thickness of the piezoelectric film can be, for example, within the range of 5 to 3000 μm, within the range of 5 to 2500 μm, within the range of 5 to 2000 μm, within the range of 5 to 1500 μm, within the range of 5 to 1000 μm, within the range of 5 to 800 μm, within the range of 5 to 500 μm, within the range of 5 to 200 μm, within the range of 5 to 100 μm, or within the range of 5 to 60 μm. A preferable film thickness can vary depending on the use of the piezoelectric film.

Variation Coefficient of Film Thickness
Method for Determining Variation Coefficient of Film Thickness In the present specification, the variation coefficient of thickness is defined as the variation coefficient of values measured at 10 points every square centimeter over the entire film in the plane direction.

The variation coefficient of the thickness of the piezoelectric film can be preferably 10% or less, and more preferably 5% or less.

Retardation
Method for Determining Retardation

In the present specification, the retardation is determined by measurement with a retardation film and material evaluation system (product name: RETS-100, Otsuka Electronics Co., Ltd.) or a similar instrument using a sample of the film cut to a size of 2 cm×2 cm or more. In the present specification, a value of 550 nm is adopted as the numerical value of retardation.

The lower limit of the retardation of the piezoelectric film is not limited, and can be, for example, 0.5 nm, 1 nm, 2 nm, 4 nm, 5 nm, or 10 nm.

The upper limit of the retardation of the piezoelectric film can be, for example, 5000 nm, 4500 nm, 4000 nm, 3500 nm, 3000 nm, 2500 nm, 2000 nm, 1500 nm, 1000 nm, 500 nm, 400 nm, or 300 nm.

The retardation of the piezoelectric film is preferably within the range of 0.5 to 500 nm, more preferably within the range of 0.5 to 400 nm, and even more preferably within the range of 1 to 400 nm.

Ratio of Retardation [Nm]/Film Thickness [Mm]

The ratio of retardation [nm]/film thickness [μm] is a value obtained by dividing the retardation determined by the above method by the film thickness determined by the above method.

The lower limit of the ratio can be, for example, 0.02, 0.05, or 0.1.

The upper limit of the ratio can be, for example, 2.5, 2.0, or 1.5.

The ratio can be, for example, within the range of 0.02 to 2.5 or within the range of 0.05 to 2.0.

Use

The piezoelectric film can be applied to various uses. Specific examples of uses include sensors (e.g. touch sensors, vibration sensors, biosensors, and tire sensors (sensors installed on the inner surface of tires)), actuators, touch panels, haptic devices (devices that have the ability to feed back tactile sensations to users), vibration power generators (e.g., vibration power floors and vibration power tires), speakers, and microphones. Among these uses, the piezoelectric film, which has high dimensional stability due to heat, can be preferably used for piezoelectric materials whose production process includes heat treatment.

Production Method

The piezoelectric film according to one embodiment of the present disclosure can be produced, for example, by a production method comprising:

step A of preparing an unstretched and non-polarized polymer film (e.g., a non-polarized vinylidene fluoride/tetrafluoroethylene copolymer film) by a casting method;

step B of polarizing the unstretched and non-polarized polymer film; and step C of optionally heat-treating the unstretched polymer film at any time from step B.

Step A: Film Preparation Step

The method for producing the unstretched and non-polarized polymer film by a casting method comprises, for example:

(1) dissolving or dispersing the vinylidene fluoride/tetrafluoroethylene copolymer and the desired components mentioned above (e.g., inorganic oxide particles and an affinity improver) in a solvent to prepare a liquid composition;

(2) applying (casting or coating) the liquid composition to a substrate; and (3) exposing the substrate, to which the liquid composition has been applied, to a predetermined temperature to form a film.

These steps are preferably performed by a roll-to-roll process, in terms of industrial productivity.

The dissolution temperature in the preparation of the liquid composition is not limited, but is preferably room temperature to 80° C. from the standpoint of promoting dissolution and preventing film coloring.

Preferable examples of the solvent, from the standpoint of coloring prevention, include ketone solvents (e.g., methyl ethyl ketone (MEK), methyl isobutyl ketone (MIBK), acetone, diethyl ketone, dipropyl ketone, and cyclohexanone), ester solvents (e.g., ethyl acetate, methyl acetate, propyl acetate, butyl acetate, and ethyl lactate), ether solvents (e.g., tetrahydrofuran, methyltetrahydrofuran, and dioxane), and amide solvents (e.g., dimethylformamide (DMF) and dimethylacetamide). These solvents may be used singly or in a combination of two or more. The amount of the amide solvent contained in the solvent is preferably 50 mass % or less.

The liquid composition may be cast (or applied) onto a substrate according to a commonly used method, such as knife coating, cast coating, roll coating, gravure coating, blade coating, rod coating, air doctor coating, or slot die.

Of these, gravure coating or slot die is preferable from the standpoint of easy handling, less irregular thickness of the resulting film, and excellent productivity.

Examples of usable substrates include polyethylene terephthalate (PET) films.

The substrate to which the liquid composition has been applied may be exposed to a predetermined temperature according to a general heat treatment (or heat drying) method for film formation. The heat treatment (or heat drying) is preferably performed, for example, by passing the substrate to which the liquid composition has been applied through a high-temperature furnace (or drying furnace) by a roll-to-roll process.

The substrate to which the liquid composition has been applied is preferably exposed to a predetermined temperature in two or more stages (e.g., within the range of 2 to 4 stages, preferably 2 or 3 stages, and more preferably 2 stages).

The exposure preferably includes a stage of exposing the substrate to a first temperature and a stage of exposing the substrate that has been exposed to the first temperature to a second temperature lower than the first temperature.

The stage of exposure to the first temperature can be, for example, a stage of evaporating the solvent of the liquid composition. The first temperature (or drying temperature) is, for example, within the range of 150 to 230° C., preferably within the range of 155 to 220° C., more preferably within the range of 160 to 210° C., and even more preferably within the range of 165 to 200° C. The time of exposure to the first temperature (or drying time) is preferably short, more preferably less than 1 hour, and even more preferably 0.8 hours or less (e.g., within the range of 0.3 to 0.8 hours).

The stage of exposure to the second temperature can be, for example, a stage of crystallization and a stage of crystal growth (increasing the degree of crystallinity). The second temperature is not limited as long as it is lower than the first temperature. For example, the second temperature is within the range of 60° C. or more and less than 150° C., preferably within the range of 80 to 145° C., more preferably within the range of 100 to 140° C., and even more preferably within the range of 110 to 135° C. The time of exposure to the second temperature is preferably long, for example, 1 hour or more, preferably 2 hours or more, more preferably 3 hours or more, even more preferably 4 hours or more, still even more preferably 5 hours or more, and particularly preferably 6 hours or more.

In particular, the exposure is preferably performed at a temperature within the range of 150 to 200° C. for a short period of time (e.g., less than 1 hour, and preferably 0.3 to 0.8 hours), and then at a temperature within the range of 110° C. or more and less than 150° C. for a long period of time (e.g., 5 hours or more, and preferably 6 hours). This treatment can form a piezoelectric film that not only has a large residual polarization amount but also satisfies other physical properties, such as internal haze value and degree of crystallinity.

The thickness of the non-polarized film prepared in step A may be set according to the piezoelectric film to be obtained.

Step B: Polarization Treatment Step

The non-polarized copolymer film (hereinafter, may be simply referred to as "non-polarized film") used in step B is preferably an unstretched film.

The polarization treatment in step B can be performed by a commonly used method, preferably corona discharge treatment.

Although either negative corona or positive corona may be used for corona discharge, negative corona is preferably used because of the ease of polarization of non-polarized films.

The corona discharge treatment is not limited. The treatment can be performed, for example, by applying voltage to a non-polarized film using linear electrodes as described in JP2011-181748A; by applying voltage to a non-polarized film using needle-shaped electrodes; or by applying voltage to a non-polarized film using grid electrodes.

The conditions for the corona discharge treatment may be suitably set based on common knowledge in the art. If the conditions for the corona discharge treatment are overly weak, the obtained piezoelectric film may have insufficient piezoelectricity. On the other hand, if the conditions for the corona discharge treatment are overly strict, the obtained piezoelectric film may have point-like defects.

In order to suppress the in-plane variation of the piezoelectric constant $d_{33}$ of the obtained polarized film, it is desirable that the distance between each needle-shaped electrode and/or linear electrode and the film is constant; that is, it is desirable that there is no (or extremely small) in-plane variation in the distance between each electrode and the film (specifically, the difference between the longest distance and the shortest distance is preferably within 6 mm, more preferably within 4 mm, and even more preferably within 3 mm).

In addition, for example, when voltage is continuously applied by a roll-to-roll process, it is desirable that the film is brought into close contact with the roll appropriately and uniformly by applying a constant tension to the film.

For example, when voltage is continuously applied using linear electrodes by a roll-to-roll process, the direct current electric field is within the range of, for example, −15 to −25 kV; however, this varies depending on the distance between the linear electrodes and the non-polarized film, the film thickness, and the like. The rate of treatment is within the range of, for example, 10 to 1200 cm/min.

Alternatively, the polarization treatment may be performed, for example, by applying voltage to the non-polarized film with the film sandwiched between plate electrodes. More specifically, when voltage is applied to the non-polarized film with the film sandwiched between plate electrodes, the following conditions, for example, may be applied: a direct current electric field within the range of 0 to 400 MV/m (preferably 50 to 400 MV/m), and a voltage application time within the range of 0.1 seconds to 60 minutes.

Step C: Heat Treatment Step

Step C is optionally performed at any time from step B. More specifically, step C may be performed before step B, simultaneously with step B, or after step B. When step C is performed after step B, the heat treatment in step C can be performed on the polarized film obtained in step B or a part in which polarization has been completed in step B. More specifically, while the polarization treatment in step B is performed, the heat treatment in step C may also be performed on the part in which the polarization treatment has been completed.

The method for the heat treatment is not limited, and may be performed, for example, by sandwiching the unstretched polymer film (hereinafter, may be simply referred to as "the film") between two metal plates and heating the metal plates; heating a roll of the film in a constant-temperature chamber; heating a metal roll and bringing the film into contact with the heated metal roll in the production of the film by a roll-to-roll process; or passing the film through a heated oven by a roll-to-roll process. When step C is performed after step B, the polarized film may be heat-treated singly, or the film may be stacked on another type of film or a metal foil to form a laminated film and the laminated film may be heat-treated. In particular, when the heat treatment is performed at high temperatures, the latter method is preferable because wrinkles are less likely to be formed in the polarized film.

The temperature for the heat treatment may vary depending on the type of polarized film to be heat-treated, and is preferably within the range of the melting point of the polarized film to be heat-treated−100° C. to the melting point of the polarized film to be heat-treated+40° C.

More specifically, the temperature for the heat treatment is preferably within the range of 80° C. or more, more preferably 85° C. or more, and even more preferably 90° C. or more.

The temperature for the heat treatment is also preferably within the range of 170° C. or less, more preferably 160° C. or less, and even more preferably 140° C. or less.

The time for the heat treatment is typically within the range of 10 seconds or more, preferably 0.5 minutes or more, more preferably 1 minute or more, and even more preferably 2 minutes or more.

The upper limit of the time for the heat treatment is not limited, and the time for the heat treatment is typically within the range of 60 minutes or less.

The conditions for the heat treatment are preferably such that the temperature for the heat treatment is within the range of 90° C. or more, and the time for the heat treatment is within the range of 1 minute or more.

After the heat treatment, the film is generally cooled to a predetermined temperature. The temperature is preferably within the range of 0° C. to 60° C., and may be room temperature. The cooling rate may be gradual or rapid, and rapid cooling is preferable from the standpoint of productivity. Rapid cooling can be performed, for example, by means such as blown air. In the present specification, the heat treatment of the film described above is also referred to as "annealing treatment."

The piezoelectric film obtained in this manner has high piezoelectricity even after annealing treatment, and even after production of a piezoelectric material whose production process includes heat treatment.

Roll of Piezoelectric Film

The piezoelectric film can be preferably stored and shipped as a roll.

The roll of the piezoelectric film according to one embodiment of the present disclosure may consist of the piezoelectric film, may have a form in which the piezoelectric film laminated with a protective film or the like is wound, or may comprise a core of a paper tube or the like and the piezoelectric film wrapped around the core.

The roll of the piezoelectric film preferably has a width within the range of 50 mm or more and a length within the range of 20 m or more.

The roll of the piezoelectric film can be prepared, for example, by winding the piezoelectric film using an unwinding roller and a winding roller.

From the standpoint of suppressing the deflection of the film, it is preferable to set the unwinding roller and the winding roller parallel to each other, as is usually performed.

In order to improve the slipperiness of the film, the roller preferably used is a roller with good slipperiness, specifically a roller coated with a fluororesin, a plated roller, or a roller coated with a release agent.

The uneven thickness of the film causes unevenness in the thickness of the roll, such as "high edge" (the end of the roll is thicker than the axial center of the roll; when the film thickness at both ends is lower than that in the center, the both ends are recessed compared to the center; or when the thickness changes in an inclined manner from one end to the other, the end with a lower film thickness is recessed), which may cause the formation of wrinkles. This may also cause deflection of the film (curve in a state in which no tension other than the tension due to gravity is applied) when the film is unwound.

In general, for the purpose of preventing the high edge of the roll, the edge of the film, which is the edge of the roll, is slit using a slitter. When the thickness of the film is uneven over a wide range from the edge of the film, it is difficult to prevent the high edge of the roll and deflection only by slitting the edge.

Further, in general, the high edge, recesses, and deflection are more likely to occur in films that are wider (e.g., 100 mm or more) and longer (e.g., 50 m or more). However, since the piezoelectric film has a highly uniform thickness, even when the film is wide (e.g., 100 mm or more) and long (e.g., 50 m or more), the high edge, recesses, and deflection can be suppressed in the resulting roll without any treatment on the film or simply by slitting the edge of the film, which is the edge of the roll, using a slitter.

The edges (film edges) removed by slitting can be collected and recycled as a raw material for the piezoelectric film.

The roll of the piezoelectric film has a highly uniform thickness. The ratio of the thickness of the roll at the thicker end to the thickness of the roll in the axial center is preferably within the range of 70 to 130%. This can suppress the deflection of the film unwound from the roll of the piezoelectric film.

Further, it is preferable that at least the surface material of the rollers used for producing the piezoelectric film and the roll thereof is polytetrafluoroethylene (PTFE), chrome plating, or stainless steel (SUS).

As a result, wrinkles on the film can be suppressed.

Piezoelectric Material

The piezoelectric material according to one embodiment of the present disclosure is a laminate, which comprises the piezoelectric film and an electrode provided on at least one surface of the piezoelectric film.

Specific examples of the electrode include indium tin oxide (ITO) electrodes, tin oxide electrodes, metal nanowires, metal nanoparticles (e.g., silver nanoparticles), and organic conductive resins.

The piezoelectric material may be a laminate comprising the piezoelectric film, a positive electrode layer (or an upper electrode layer) provided on one surface of the piezoelectric film, and a negative electrode layer (or a lower electrode layer) provided on the other surface of the piezoelectric film.

The piezoelectric material may have an insulating layer on the surface of the electrode layer on which the piezoelectric film is not laminated. The piezoelectric material may also have a cover (e.g., an electromagnetic shielding layer) on the surface (or top surface) of the electrode layer on which the piezoelectric film is not laminated.

The method for producing the piezoelectric material comprises, for example:

preparing the piezoelectric film; and providing an electrode on at least one surface of the piezoelectric film.

In the step of providing an electrode, the method of forming the electrode generally includes heat treatment. Specific examples include a method of forming a film from an electrode material by a physical vapor deposition method (e.g., vacuum evaporation, ion plating, or sputtering) or by a chemical vapor deposition method (e.g., plasma CVD), and a method of applying an electrode material to a substrate.

The lower limit of the temperature for the heat treatment is, for example, 25° C., preferably 40° C., and more preferably 50° C.

The upper limit of the temperature for the heat treatment is the melting point of the polarized film to be heat-treated– 3° C., for example, 220° C., preferably 180° C., more preferably 150° C., and even more preferably 130° C.

The temperature for the heat treatment can be within the range of, for example, 25 to 220° C., and preferably within the range of 40 to 130° C. The reduction of piezoelectricity can be significantly suppressed by performing heat treatment at such temperatures.

The time for the heat treatment is generally within the range of 10 seconds or more, preferably 1 minute or more, more preferably 10 minutes or more, and even more preferably 15 minutes or more.

EXAMPLES

One embodiment of the present disclosure is described in more detail below with reference to Examples; however, the present disclosure is not limited thereto.

The following electrodes were used in the Examples and Comparative Examples described later.
Electrodes Used
(1) A needle-shaped electrode rod with electrode needles (needle-shaped electrodes) (R=0.06 mm; produced by Morita Seishinsyo Co., Ltd.) arranged in a row at 10-mm intervals on the center line of a 20-mm-wide (10-mm-thick, 500-mm-long) brass rod.
(2) As in (1), a needle-shaped electrode rod with electrode needles (R=0.06 mm; produced by Morita Seishinsyo Co., Ltd.) arranged in a row at 15-mm intervals.
(3) A gold-plated tungsten linear electrode with a diameter of 0.1 mm (length: 500 mm)

In piezoelectric films described later, the residual polarization amount, internal haze value, degree of crystallinity, variation coefficient of thickness, piezoelectric constant $d_{33}$ and retardation were measured by the following methods.
Residual Polarization Amount An aluminum electrode (flat electrode) was patterned by vacuum vapor deposition on the center (5 mm×5 mm) of a sample film cut to 20 mm×20 mm. Two lead electrodes (3 mm×80 mm) made of aluminum foil reinforced with insulating tape were attached to the flat electrode with conductive double-sided tape. The sample film, a function generator, a high-voltage amplifier, and an oscilloscope were incorporated into a Sawyer-Tower circuit, and a triangular wave was applied to the sample film (maximum: ±10 kV). The response of the sample film was measured using the oscilloscope to determine the residual polarization amount at an applied electric field of 120 MV/m.
Internal Haze Value The film was inserted into a quartz cell filled with water, and the internal haze value was measured according to ASTM D1003 using NDH7000SP CU2II (product name, Nippon Denshoku Industries Co., Ltd.).
Degree of Crystallinity A film sample was placed directly on a sample holder with an aperture, and X-ray diffraction measurement was performed at a diffraction angle 2θ of 10 to 40°. In the obtained X-ray diffraction pattern, a baseline was set as a straight line connecting a diffraction intensity at a diffraction angle 2θ of 10° and a diffraction intensity at a diffraction angle 2θ of 25°. The area surrounded by the baseline and a diffraction intensity curve was separated into two symmetric peaks by profile fitting. Of these peaks, the one with a larger diffraction angle 2θ was recognized as a crystalline peak, and the one with a smaller diffraction angle 2θ was recognized as an amorphous halo peak.

The degree of crystallinity was calculated by 100×(area of crystalline peak)/(sum of area of crystalline peak and area of amorphous halo peak).

Variation Coefficient of Thickness

The thickness was measured at 10 points every square centimeter over the entire film in the plane direction to calculate the variation coefficient of the thickness of the film.

The average of 10 measured points was taken as the average thickness, and the variation coefficient of thickness was calculated using the following formula:

Variation coefficient of thickness (%)=±[(maximum thickness−average thickness)+(average thickness−minimum thickness)]/average thickness/2× 100

Piezoelectric Constant $d_{33}$

The piezoelectric constant was measured using a piezometer system (PM300, Piezotest). In this measurement, a sample was clipped at 1 N, and the charge generated by applying a force of 0.25 N at 110 Hz was read.
Retardation The retardation was determined by measurement with a retardation film and material evaluation system (product name: RETS-100, Otsuka Electronics Co., Ltd.) using a film sample cut to a size of 2 cm×2 cm or more. A value of 550 nm was adopted as the numerical value of retardation.
(1) Production of Piezoelectric Films
Piezoelectric Film 1

A piezoelectric film 1 having a film thickness of 40 μm and an area of 50 m² was prepared by a roll-to-roll process. Specifically, the piezoelectric film 1 was obtained by spreading a methyl ethyl ketone solution of 24 wt % vinylidene fluoride/tetrafluoroethylene copolymer (molar ratio 80:20) on a PET base film fed from a roll, evaporating the solvent by treatment at 190° C. for 0.5 hours, then lowering the temperature to 120° C. and holding it for 6 hours, and then cooling it to room temperature, followed by polarization treatment described below.
Piezoelectric Film 2

A piezoelectric film 2 having a film thickness of 40 μm and an area of 50 m² was prepared by a roll-to-roll process. Specifically, the piezoelectric film 2 was obtained by spreading a methyl ethyl ketone solution of 24 wt % vinylidene fluoride/tetrafluoroethylene copolymer (molar ratio 80:20) on a PET base film fed from a roll, evaporating the solvent by treatment at 190° C. for 0.5 hours, then lowering the temperature to 120° C. and holding it for 1 second, and then cooling it to room temperature, followed by polarization treatment described below.
Piezoelectric Film 3

A piezoelectric film 3 having a film thickness of 40 μm and an area of 50 m² was prepared by a roll-to-roll process. Specifically, the piezoelectric film 3 was obtained by spreading a methyl ethyl ketone solution of 24 wt % vinylidene fluoride/tetrafluoroethylene copolymer (molar ratio 80:20) on a PET base film fed from a roll, evaporating the solvent by treatment at 190° C. for 0.5 hours, then lowering the temperature to 120° C. and holding it for 5 hours, and then cooling it to room temperature, followed by polarization treatment described below.
Polarization Treatment In an ISO class 7 clean room (humidity: 60%), as outlined in FIG. 1, a vinylidene fluoride/tetrafluoroethylene copolymer film 2 (hereinafter, may be simply referred to as "film 2") having a width of 550 mm, a length of 200 m, and a film thickness (20 to 40 μm) shown in Table 1 was mounted on a SUS ground electrode, which was a grounded roller 1 (diameter: 200 mm, width: 800 mm), so that the film moved along the roller 1 at a wrap angle of 200°. Needle-shaped electrodes were placed as a first electrode E1 so that the line of the needle-shaped electrodes was perpendicular to the surface of the roller 1 (i.e., in the moving radius direction of the roller 1) and so that the tip of the needle-shaped electrodes (first electrode E1) was placed at a distance of 10 mm above the film 2. The first electrode E1 was connected to a first high-voltage power supply V1. Further, at a distance of 100 mm and at a distance of 150 mm, as the length of the film 2, from the needle-shaped electrodes (first electrode E1), single gold-plated tungsten linear electrodes (length: 550 mm) with a diameter of 0.1 mm were each placed as second electrodes E2 at a distance of 20 mm above the film 2. Each of the second electrodes E2 was connected to a second high-voltage power supply V2.

After applying a voltage of −10 kV to the needle-shaped electrodes (first electrode E1) and a voltage of −10 to −15 kV to the linear electrodes (second electrodes E2), the film 2 was moved in the direction of the arrows in FIG. 1 at a speed of 96 cm/min, and allowed to pass under the tip of the needle-shaped electrodes (first electrode) and the subsequent corona discharge generated by the linear electrodes (second electrodes). Further, the film 2 was brought into contact with a grounded metal roll 3 (diameter: 70 mm) to remove the electricity from the film. Then, using a slitter, both ends of the film 2 were removed by 0.5 cm in width, and the obtained polarized film was wound around a cylindrical core having a diameter of 6 inches with a PET film sandwiched between them. The polarized film was thus produced.

The distance between the needle-shaped electrodes (first electrode E1) and the film 2, and the distance between each linear electrode (second electrode E2) and the film 2 were adjusted so that they were all constant (the difference between the longest distance and the shortest distance between each electrode and film was 0 mm).

(2) Evaluation of Piezoelectric Films

The evaluation results of the piezoelectric films 1 to 3 are shown in the following Table 1.

TABLE 1

|  | Piezoelectric film 1 | Piezoelectric film 2 | Piezoelectric film 3 |
| --- | --- | --- | --- |
| Residual polarization amount | 56 mC/m$^2$ | 28 mC/m$^2$ | 48 mC/m$^2$ |
| Internal haze value | 74% | 0.6% | 51% |
| Degree of crystallinity | 67% | 26% | 58% |
| Variation coefficient of thickness | 1.7% | 0.7% | 1.1% |
| Piezoelectric constant d$_{33}$ | −19 pC/N | −10 pC/N | −18 pC/N |
| Retardation | 26 nm | 24 nm | 40 nm |

The invention claimed is:

1. A piezoelectric film comprising a vinylidene fluoride/tetrafluoroethylene copolymer film and having a residual polarization amount of 40 mC/m$^2$ or more, wherein a ratio of internal haze value [%]/film thickness [μm] is more than 1.0, and
    wherein the residual polarization amount is determined based on a measured response when a sample is provided and an electric field of 120 MV/m is applied, the sample being an aluminum flat electrode patterned by vacuum deposition on a center of the piezoelectric film and having two lead electrodes attached thereto with conductive double-sided tape.

2. The piezoelectric film according to claim 1, wherein the residual polarization amount is 45 mC/m$^2$ or more.

3. The piezoelectric film according to claim 1, wherein the ratio of internal haze value [%]/film thickness [μm] is 1.1 or more.

4. The piezoelectric film according to claim 1, which has an internal haze value of more than 30%.

5. The piezoelectric film according to claim 1, which has an internal haze value of 40% or more.

6. The piezoelectric film according to claim 1, which has an internal haze value of 45% or more.

7. The piezoelectric film according to claim 1, which has an area of 9 cm$^2$ or more.

8. The piezoelectric film according to claim 1, wherein the residual polarization amount is 50 mC/m$^2$ or more, an internal haze value is within a range of more than 50% and 80% or less, and an area of the piezoelectric film is 9 cm$^2$ or more.

9. The piezoelectric film according to claim 1, which has a thickness of 5 to 3000 μm.

10. The piezoelectric film according to claim 1, which has an internal haze value within a range of 60 to 80%.

11. The piezoelectric film according to claim 1, which has an internal haze value within a range of 65 to 80%.

12. The piezoelectric film according to claim 1, wherein in the vinylidene fluoride/tetrafluoroethylene copolymer, a molar ratio of repeating units derived from vinylidene fluoride and repeating units derived from tetrafluoroethylene is within a range of 60/40 to 97/3.

13. The piezoelectric film according to claim 1, wherein a ratio of retardation [nm]/film thickness [μm] is within a range of 0.02 to 2.5.

14. The piezoelectric film according to claim 1, for use in one or more members selected from a group consisting of sensors, actuators, touch panels, haptic devices, vibration power generators, speakers, and microphones.

15. A piezoelectric material that is a laminate, the piezoelectric material comprising:
    the piezoelectric film according to claim 1, and
    an electrode provided on at least one surface of the piezoelectric film.

* * * * *